United States Patent
Lechelt-Kunze et al.

[11] Patent Number: 6,164,012
[45] Date of Patent: Dec. 26, 2000

[54] BIOLOGICAL MATERIAL EMBEDDED IN HYDROGELS, A PROCESS FOR THE EMBEDDING THEREOF, AND ITS USE AS ARTIFICIAL SEED

[75] Inventors: Christa Lechelt-Kunze, Köln; Joachim Simon, Düsseldorf; Werner Zitzmann, Leverkusen; Jochen Kalbe, Leichlingen; Hanns-Peter Müller, Odenthal; Rainhard Koch, Köln, all of Germany

[73] Assignee: Bayer Aktiengesellschaft, Leverkusen, Germany

[21] Appl. No.: 09/230,379

[22] PCT Filed: Jul. 21, 1997

[86] PCT No.: PCT/EP97/03906

§ 371 Date: Apr. 27, 1999

§ 102(e) Date: Apr. 27, 1999

[87] PCT Pub. No.: WO98/05197

PCT Pub. Date: Feb. 12, 1998

[30] Foreign Application Priority Data

Aug. 2, 1996 [DE] Germany ............................ 196 31 320

[51] Int. Cl.$^7$ ................................ A01H 4/00; A01C 1/06
[52] U.S. Cl. ........................................................... 47/57.6
[58] Field of Search ........................................ 47/57.6, 58.1

[56] References Cited

U.S. PATENT DOCUMENTS

| | | | |
|---|---|---|---|
| Re. 32,476 | 8/1987 | Kistner .............................. | 47/58.1 X |
| 3,734,987 | 5/1973 | Hamrin .................................. | 264/54 |
| 3,808,740 | 5/1974 | Porter et al. ......................... | 47/58.1 |
| 3,901,838 | 8/1975 | Clendinning et al. ................ | 47/9 X |
| 3,905,923 | 9/1975 | Klug . | |
| 3,920,436 | 11/1975 | Janssen ............................ | 47/57.6 X |
| 3,921,333 | 11/1975 | Clendinning et al. . | |
| 3,923,729 | 12/1975 | Clendinning et al. . | |
| 4,238,523 | 12/1980 | Porter et al. ....................... | 47/57.6 X |
| 4,251,952 | 2/1981 | Porter et al. ........................ | 47/57.6 |
| 4,285,720 | 8/1981 | Scher .................................... | 71/88 |
| 4,562,663 | 1/1986 | Redenbaugh ......................... | 47/58 |
| 4,583,320 | 4/1986 | Redenbaugh ......................... | 47/57.6 |
| 4,634,672 | 1/1987 | Baumgarten et al. ................. | 435/182 |
| 4,681,851 | 7/1987 | Baumgarten et al. ................. | 435/262 |
| 4,715,143 | 12/1987 | Redenbaugh et al. ................ | 47/57.6 |
| 4,777,762 | 10/1988 | Redenbaugh et al. ................ | 47/57.6 |
| 4,779,376 | 10/1988 | Redenbaugh .......................... | 47/57.6 |
| 5,190,797 | 3/1993 | Thaler et al. ........................ | 427/385.5 |
| 5,294,549 | 3/1994 | Pullman et al. ..................... | 435/240.45 |
| 5,321,064 | 6/1994 | Vaidya et al. ......................... | 524/56 |
| 5,334,530 | 8/1994 | Woods et al. ........................ | 435/240.48 |
| 5,662,960 | 9/1997 | Hostettler et al. .................... | 427/2.3 |
| 5,902,745 | 5/1999 | Butlet et al. ........................ | 435/297.2 |
| 5,961,906 | 10/1999 | Miller et al. ......................... | 264/109 |
| 6,032,412 | 3/2000 | Bohne et al. .......................... | 47/58.1 |

FOREIGN PATENT DOCUMENTS

| | | |
|---|---|---|
| 0 141 374 | 5/1985 | European Pat. Off. . |
| 0 571 748 | 12/1993 | European Pat. Off. . |
| 92/07457 | 5/1992 | WIPO . |
| 92/17422 | 10/1992 | WIPO . |
| 95/19102 | 7/1995 | WIPO . |
| 96/35733 | 11/1996 | WIPO . |

*Primary Examiner*—Michael J. Carone
*Assistant Examiner*—Jeffrey L. Gellner
*Attorney, Agent, or Firm*—Joseph C. Gil; N. Denise Brown

[57] ABSTRACT

The invention relates to a completely biodegradable hydrogel comprising polyester polyurethane polyurea containing urea groups as well as polysaccharides and/or their derivatives, the hydrogel containing plant material capable of dividing. The invention also relates to a process for the embedding of the biological material and the fabrication and shaping of the hydrogels from aqueous solutions. The hydrogels according to the invention may be used as coating material for embedding biological material capable of dividing, especially plant material, preferably plant cells, protoplasts, plant tissues and plant organs, as well as zygotic or somatic plant embryos, under sterile conditions for the purpose of protecting the material during storage, transport and handling. The hydrogels according to the invention may also contain further additives, for example, plant protection agents or nutrients. The embedded biological plant material according to the invention may be used as artificial seed.

14 Claims, No Drawings

BIOLOGICAL MATERIAL EMBEDDED IN HYDROGELS, A PROCESS FOR THE EMBEDDING THEREOF, AND ITS USE AS ARTIFICIAL SEED

The present invention relates to a completely biodegradable hydrogel comprising polyester polyurethane polyurea as well as polysaccharides and/or their derivatives, and plant material capable of dividing.

The invention also relates to a process for embedding the biological material and for producing and shaping the hydrogels from aqueous solutions, as well as the use of the biological material embedded in hydrogels as artificial seed.

Plants are propagated sexually via seeds and asexually or vegetatively via meristems of the plants. Both types of propagation are of great economic importance. Whereas sowing of natural seeds is largely carried out mechanically, vegetative propagation involves much manual labour and is therefore more time-consuming, labour-intensive and accordingly more expensive than propagation by seeds.

Plant species, strains, cultivars and lines in which a specific genetic constitution is important (eg. clonal propagation of elite plants) are propagated vegetatively. Vegetative propagation is also used for plants that form seeds only after a long vegetation period, that form only a few seeds, or the germination capacity of whose seeds is damaged.

In order to simplify vegetative plant propagation, in addition to the development of automated processes for large-scale cultivation, suitable substances and processes for encapsulating the fragile material, which furthermore act as a seed case, are also desirable.

In the case of some types of plants it is now possible to produce miniaturised and regenerable plants (tissues) capable of dividing in large-scale cultivation processes (eg. WO95/19102, U.S. Pat. No. 5,294,549, U.S. Pat. No. 5,334,530). Without mechanical protection and/or protection against desiccation, these plant parts can be transported and stored only to a limited extent. It is therefore desirable to encapsulate or cover plant parts as discrete units so that they can be stored and/or transported, adequately dosed, and used just like natural plant seeds.

DE 2 103 873, EP 141 374, EP 107 141, U.S. Pat. No. 4,562,663, WO 8502972, U.S. Pat. No. 4,779,376, WO 9207457 describe the embedding of plant material in hydrogels which have been produced from ionically crosslinkable polysaccharides such as alginate, gelatins, carragheens or locust bean gum.

The aforementioned materials, combinations of materials and processes according to the prior art have not up to now been completely satisfactory since in some cases they neither impart a sufficient mechanical stability to the coated structures, nor do they protect the plant tissue against a too rapid or too extensive loss of water under conditions of use. This is true in particular of the aforementioned polysaccharide derivatives. During desiccation a marked shrinkage of the materials is also observed, which can seriously affect the protective function of the seed case. A further problem specifically involving the hitherto employed coatings based on polysaccharides such as alginic acids or their salts, or further ionic polysaccharide derivatives, is the insufficient degree of rehydration after a period of desiccation. These materials can therefore be preserved only under appropriate atmospheric humidity levels.

Subsequently applied coatings of fats, oils, waxes or water-insoluble polymers in order to retard dehydration and mechanical stabilisation, as are disclosed for example in U.S. Pat. No. 4,562,663, WO 9217422, U.S. Pat. No. 5,190,797, are also unsuitable if they have to be processed under unphysiologically high temperatures, require the use of organic solvents, or if they adversely affect the oxygen supply of the enclosed biological material.

Besides hydrogels based on polysaccharides, polyurethane (PU) hydrogels have also been described. DE 3312578 and DE 4 217 891 describe the use of polyurethanes to immobilise cells capable of dividing. In this application PU hydrogels serve as carrier material of cells and biocatalysts in aqueous suspensions, although the PU hydrogels described for this purpose are not biodegradable.

The object of the present invention is to provide a form of encapsulation/packaging of biological material capable of dividing for the purposes of protecting said material during storage, transport and handling, which greatly retards desiccation, is dimensionally stable, is reswellable to a sufficient extent after partial desiccation, is biodegradable, and is easy to produce.

The addition of additives such as nutrients or active and protective substances should also be possible.

The requisite material must be able to be handled under sterile conditions and avoid the use of toxic solvents or physiologically unacceptable conditions.

The aforedescribed objects are surprisingly achieved by the use of completely biodegradable polyester polyurethane polyureas in combination with polysaccharides or polysaccharide derivatives, which may be used as dispersions in water or as aqueous solutions.

It has surprisingly been found that polyester polyurethane polyureas are suitable for coating biological materials and can be used in combination with biodegradable polysaccharides or their derivatives for the embedding in accordance with the invention within the context of the aforedescribed object of the invention.

The present invention relates to biodegradable hydrogels containing at least

A) a polyester polyurethane polyurea, as well as

B) polysaccharides and/or polysaccharide derivatives, and

C) biological material, preferably plant material capable of dividing, especially plant cells, callus tissues, protoplasts, plant tissues or plant organs, for example adventitious shoots, micronodules, axillary buds, apical buds, scions, as well as zygotic or somatic embryos or protocorm analogues.

The plant material may be derived from the following plants: Plants providing nutritional and raw materials, for example cereals (rice, maize, wheat, barley, rye, millet), potatoes, legumes (e.g. lucerne and soybeans), rapeseed, sunflowers, oil palms, sugar cane, sugar beet, sisal, cotton, miscanthus and tobacco; vegetables and root plants (e.g. tomatoes, varieties of cabbage, lettuce, carrots, aubergines, melons, gherkins, asparagus, onions, parsley, ginger); medicinal plants such as ginseng, belladonna, digitalis; fruit (e.g. apples, pears, cherries, grapes, strawberries, citrus fruits, mango, papaya, bananas, nuts); tea, cocoa, coffee bushes; forest trees, for example conifers such as spruce, fir, pine, larch; foliage trees, for example poplar, beech, oak; ornamental plants, for example roses, chrysanthemums, lillies, amaryllis, orchids, geraniums, begonias, pinks, anthurium.

Furthermore, there may preferably be used such biological materials capable of division, which are particularly preferably derived from transgenic plants, in which propagation through seeds or through vegetative organs is no longer possible or possible only with difficulty on account of the nature of the gene technology alteration, e.g. through seed-specific or nodule specific expression of the products.

Hereinafter the term "embedding" describes all possible processes of encapsulation, covering, coating, packaging, etc. of the biological material according to the invention.

The biodegradability of materials is oriented to the requirements under standard conditions (see Example 6).

According to the invention the polyester polyurethane polyureas may be used mixed with ionic or neutral biodegradable polysaccharides and their derivatives in a one-stage or multistage process, in order to form shaped bodies, e.g. spheres, fibres, sheets, coatings or the like.

A water-containing matrix (hydrogel) is formed by the polysaccharides, and the mechanical properties of the hydrogel are surprisingly improved to such an extent by the polyester polyurethane polyurea as to permit the production of simple shaped bodies, for example spheres, and the water loss of the hydrogel as well as of the biological material according to the invention can be controlled.

The polyester polyurethane polyureas used according to the invention are known from DE 19 517 185, now U.S. Pat. No. 5,961,906.

The aforementioned polyureas are prepared by reacting the following while maintaining an equivalent ratio of isocyanate groups to groups reactive with isocyanate groups, of 1:1 to 2:1 a) a diisocyanate component comprising
  a1) hexamethylene diisocyanate or
  a2) mixtures of hexamethylene diisocyanate with a total of up to 60 wt. %, referred to the mixture, of 1-isocyanato-3,3,5-trimethyl-5-isocyanatomethylcyclohexane and/or 4,4'-diisocyanatodicyclohexylmethane and/or 1-methyl-2,4(6)-diisocyanatocyclohexane with b) a diol component comprising
  b1) at least one polyester diol having a molecular weight, calculated from the hydroxyl group content, of 500 to 10000, of (i) adipic acid and/or succinic acid and (ii) at least one alkane diol with 2 to 6 carbon atoms, or
  b2) a mixture of such polyester diols having up to 32 wt. %, referred to the total weight of component b), of alkane diols optionally having ether groups and containing 2 to 6 carbon atoms, c) a diamine component in an amount of 2 to 50 equivalent %, referred to the total amount of the groups, reactive to isocyanate groups, present in the components b) and c), comprising
  c1) diaminosulphonates of the general formula $H_2N—(—CH_2—)_n—NH—(—CH_2—)_m—SO_3Me$ 

or
  c2) mixtures of diaminosulphonates c1) with up to 70 wt. %, referred to the total weight of component c), of ethylenediamine, d) optionally hydrophilic polyether alcohols of the general formula H—X—O—R 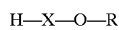

in an amount of up to 10 wt. %, referred to the total weight of the components b), c) and d), as well as e) optionally water, which is not included in the calculation of the equivalent ratio of isocyanate groups to groups reactive with isocyanate groups,
  wherein in the aforementioned general formulae
  m and n denote independently integers from 2 to 6,
  Me denotes potassium or sodium,
  R denotes a monovalant hydrocarbon radical with 1 to 12 carbon atoms, and
  X denotes a polyalkylene oxide chain in the molecular weight range 88 to 4000, whose alkylene oxide units comprise at least 40% ethylene oxide units and the remainder propylene oxide units.

Aqueous dispersions of polyester polyurethane polyureas are thus obtained.

The term "aqueous dispersion" is also intended to include aqueous solutions that may be present if the concentration of hydrophilic centres in the polyurethanes containing urea groups is sufficiently high to ensure solubility in water. Often these dispersions are aqueous systems that contain polyurethane having both dispersed and dissolved urea groups.

In order to prepare the aqueous dispersions, the aforementioned starting materials a), b), c) and optionally d) and/or optionally e) are mixed in the aforementioned quantitative ratios.

The diisocyanate component a) consists preferably exclusively of hexamethylene diisocyanate or of a hexamethylene diisocyanate mixture with a total of up to 60 wt. % of 1-isocyanato-3,3,5-trimethyl-5-isocyanatomethylcyclohexane and/or 4,4'-diisocyanatodicyclohexylmethane and/or 1-methyl-2,4(6)-diisocyanato-cyclohexane.

The diol component b) comprises either b1) at least one polyester diol or b2) a mixture of at least one polyester diol b1) with up to 32 wt. %, preferably up to 10 wt. %, of at least one alkane diol optionally containing ether groups and having 2 to 6 carbon atoms.

Suitable polyester diols b1) are those having a molecular weight, calculated from the hydroxyl group content, of 500 to 10000 preferably 1000 to 2500 based on (i) adipic acid and/or succinic acid and (ii) alkane diols optionally containing ether groups and having 2 to 6 carbon atoms, for example ethylene glycol, diethylene glycol, 1,4-butanediol, neopentyl glycol and/or 1,6-hexanediol. Particularly preferred are polyester diols in whose preparation ethylene glycol and/or 1,4-butane diol have exclusively been used as diol.

The optionally ether group-containing alkane diols with 2 to 6 carbon atoms that are optionally used as hydroxyl group-containing chain extension agents are those of the type just mentioned above by way of example.

The diamine component c) comprises either c1) diaminosulphonates of the aforementioned general formulae or c2) mixtures of such diaminosulphonates with ethylenediamine, which if used at all are employed in amounts of up to 90 equivalent %, preferably up to 70 equivalent %, referred to the amino groups of component c) that can react with isocyanate groups. Particularly preferred diaminosulphonates are the potassium or sodium salts of N-(2-aminoethyl)-2-aminoethanesulphonic acid.

The diamine component c) is generally used in an amount of 1 to 10 wt.%, preferably 2 to 5 wt. %, referred to the weight of the component b).

The structural component d) that is optionally used is a hydrophilic, monohydric polyether alcohol of the general formula H—X—O—R 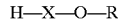

in which
  R and X have the aforementioned meanings.
  Preferred are polyether alcohols of the type in which
  R denotes an aliphatic hydrocarbon radical with 1to 4 carbon atoms, and X denotes a polyalkylene oxide chain in the molecular weight range from 500 to 4000, in which at least 40%, in particular at least 70% and particularly preferably 100% of the alkylene oxide units present are ethylene oxide units, the remaining alkylene oxide units being propylene oxide units.

The shaping and simultaneous embedding of the biological material is effected by an ionically induced coacervation of the polyester polyurethane polyurea in which the polysaccharide component is enclosed. The embedding process can be carried out in one step, or also in a multi-stage process. In the one-step process the biological material and polyester polyurethane polyurea are mixed together and coacervated by adding them to an aqueous salt solution. This inclusion process is basically determined by the viscosity of the polyester polyurethane polyurea/polysaccharide mixture used in the solvent that is employed.

In a two-stage process hydrogel spheres comprising a polysaccharide may first of all be produced by choosing a suitable polysaccharide, for example alginate. These hydrogel particles can be provided with a mechanically stable coating by immersion in an aqueous solution of the polyester polyurethane polyurea.

All biodegradable polysaccharides or their derivatives may be used individually or as a mixture as polysaccharide component of the hydrogel according to the invention. Suitable polysaccharides are for example native and soluble starches obtained from any suitable source, amyloses, amylopectin, alginic acids, alginates, carrageenan, chitin, chitosan, dextran, glycogen, guar, carob seed flour, laevan, pectin, pullulan, tamarind seed flour, xanthan and hylan, as well as cellulose obtained from any suitable source. Also suitable are cellulose derivatives, for example cellulose ethers, cellulose esters and cellulose carbamates.

Particularly suitable are for example cellulose ethers such as methyl cellulose, ethyl cellulose or benzyl cellulose with average degrees of subsitution of less than or equal to 2.5, hydroxyethyl cellulose, hydroxypropyl cellulose, dihydroxypropyl cellulose, hydroxybutyl cellulose, methylhydroxyethyl cellulose, methylhydroxypropyl cellulose, methylhydroxybutyl cellulose, ethylhydroxypropyl cellulose, ethylhydroxyethyl cellulose, carboxyalkyl cellulose, sulphoalkyl cellulose, cyanoethyl cellulose and their mixed ethers. Particularly preferred are methyl cellulose, hydroxyethyl cellulose or hydroxypropyl cellulose. Also suitable are polysaccharide derivatives, in particular cellulose derivatives with arbitrary mixtures of ether, ester and carbamate substituents.

The polyurethane polysaccharide combinations according to the invention, hereinafter termed "blend", can be sterilised by autoclaving and are fully biodegradable.

These blends also enable further properties to be monitored and adjusted, namely water content and balance, dimensional stability, permeability to oxygen and nutrients, adjustment of physiological conditions, mechanical breakdown, for example by sprouting plants, as well as the incorporation and permeability of nutrients, protective agents, and active constituents.

It must be considered surprising that the blends possess combinations of properties that are of advantage for the intended use, namely the encapsulation of biological material capable of division. Such combinations of properties include:

the blends can be processed in aqueous solvents.
the blends can be processed at physiological temperatures (18°–30° C.).
the blends can be sterilised by autoclaving without losing their properties.
the blends are fully biodegradable and can be composted.
the blends can be used in simple, economic processes for encapsulation.
the blends are non-toxic to plants.
the blends can be processed so as to ensure water and gas exchange.
the blends result in satisfactory germination rates.

The present invention also provides water-containing embedding compositions for biological material that contain a completely biodegradable polyester polyurethane polyurea and at least one completely biodegradable ionic or neutral polysaccharide or polysaccharide derivative.

The embedding composition preferably comprises at least 20 wt. % of the aforedescribed polyester polyurethane polyurea and at least 0.1 wt. % of a polysaccharide component, for example starch, a starch derivative, cellulose, a cellulose ether, or arbitrary mixtures thereof.

Water-soluble or at least readily swellable polysaccharide derivatives are preferred, for example starch, starch ethers or cellulose ethers, as well as aqueous 5–50 wt. % dispersions of the polyester polyurethane polyurea. Particularly preferred are soluble starches, alginates, methyl cellulose, hydroxyethyl cellulose, methylhydroxypropyl cellulose, methylhydroxyethyl cellulose and/or hydroxypropyl cellulose.

The invention also provides a process for embedding biological material, in which the said biological material is mixed in the presence of an aqueous dispersion of a polyester polyurethane polyurea with a polysaccharide and/or polysaccharide derivative and this mixture is coacervated by contact with an aqueous salt solution. The polysaccharide component and the added biological material are enclosed by means of this ionically induced coacervation of the polyester polyurethane polyurea, this inclusion process basically also being determined by the viscosity of the employed polyester polyurethane polyurea/polysaccharide mixture in the solvent that is used.

The kinematic viscosity of the solution to be ionically crosslinked is preferably greater than $1.1 \times 10^6$ m$^2$/sec.

The embedding process can be carried out in one step as well as in a multistage process. In the case of a one-stage process the biological material, polyester polyurethane polyurea and polysaccharide component are mixed together and the mixture is coacervated by addition to an aqueous salt solution. Hydrogel particles are formed, which depending on the process can be produced in the form of spheres, tubing, etc. The hydrogel embedding material comprises a blend of polysaccharide and polyester polyurethane polyurea.

In a two-stage process hydrogel spheres consisting of a polysaccharide can first of all be produced by choosing a suitable polysaccharide, for example alginate. These hydrogel spheres are obtained by adding a mixture of polysaccharide and biological material dropwise to a salt solution. The hydrogel particles also contain sufficient amounts of ions for the coacervation of the polyester polyurethane polyurea. These hydrogel particles may accordingly be provided with a mechanically stable coating by immersion in an aqueous solution of the polyurethane polyurea.

In principle therefore, there are at least 2 possible ways of carrying out the embedding process of the biological material in polysaccharide/polyester polyurethane polyurea hydrogels.

In general this process can be varied by altering the combined mixing of biological material, polysaccharide, polyester polyurethane polyurea and ions, the interaction of the polyester polyurethane polyurea and ions always resulting in the coacervation and thus the embedding and shaping, with the result that this stage has to be carried out last, although arbitrary mixtures of A and B can be used, where mixture A may comprise polysaccharide, polyester polyurethane polyurea and/or biological material, and mixture B may comprise ions, biological material and polysaccharide.

In a particularly preferred one-stage embodiment of the process the polysaccharide component is swelled or dissolved in an aqueous dispersion of the polyester polyurethane polyurea, the biological material is added, and the resultant mixture is coacervated by adding ions, preferably polyvalant ions, especially $Ca^{2+}$, $Mg^{2+}$, or $Al^{3+}$, in the form of their chlorides in a concentration range from 10–1000 mM, a shaping into spheres, fibres, sheets or other moulded bodies being able to be effected by this procedure. The results are hydrogels comprising a blend of polysaccharide and polyester polyurethane polyurea.

In a further preferred two-stage embodiment of the process the biological material is mixed with ions and polysaccharide in an aqueous solvent, and embedding in a polysaccharide hydrogel, which in turn is enveloped by a polyurethane polyurea coating, is carried out by adding the mixture to a polyurethane polyurea dispersion.

In the embedding process nutrients, protective substances and active agents that promote the growth or metabolism of the biological material to be embedded, and also protect the latter against harmful influences, may be added to the embedding compositions.

In a preferred embodiment the embedding composition may be prepared in a semi-concentrated nutrient medium having the composition specified by Murashige and Skoog (published in Physiol. Plant. 15, 473, 1962), to which 5–20 g/l of sucrose, but preferably 10 g/l of sucrose, have been added.

Any other nutrient salt mixtures that are for example commercially available, as well as sugar, may also be used depending on the embedded plant material. The nutrient media may contain phytohormones known to the person skilled in the art in order to influence the development. Depending on the plant material, the nutrients include the conventional and commercially available nutrient salt mixtures and vitamin mixtures as well as, optionally, likewise commercially available natural or synthetic phytohormones, for example from the class of auxins, cytokinins, gibberelins, abscisic acid, as well as ethylene-forming substances. In addition, compounds that have vitamin-like or phytohormone-like effects, for example chlorocholine chloride, lipo-oligosaccharides, salicylic acid derivatives, may also be used.

In a particular embodiment bactericidal, fungicidal, insecticidal, acaricidal, nematicidal and, in the case of appropriate natural tolerance or tolerance imparted by gene technology, also herbicidal active substances may be added to the embedding material in order to protect the dividing plant material. Protective substances include for example insecticides, for example from the class of phosphoric acid esters, carbamates, especially Imidacloprod, or for example fungicides from the classes of azoles, especially Triadimenol and Tebuconazol.

The following may be mentioned as examples of fungicides:

2-Aminobutane; 2-Anilino-4-methyl-6-cyclopropyl-pyrimidine; 2,6'-Dibromo-2-methyl-4'-trifluoromethoxy-4'-trifluromethyl- 1, 3-thiazol-5-carboxanilide; 2,6-Dichloro-N-(4-trifluoromethylbenzyl)-benzamide; (E)-2-Methoximino-N-methyl-2-(2-phenoxyphenyl)-acetamide; 8-Hydroxyquinoline sulphate; Methyl-(E)-2-{2-[6-(2-cyanophenoxy)-pyrimidin-4-yloxy]-phenyl}-3-methoxy acrylate; Methyl-(E)methoximino [alpha-(o-tolyloxy)-o-tolyl]-acetate; 2-Phenylphenol (OPP), Aldimorph, Ampropylfos, Anilazin, Azaconazol, Benalaxyl, Benodanil, Benomyl, Binapracyl, Biphenyl, Bitertanol, Blasticidin-S, Bromuconazole, Bupirimate, Buthiobate, Calcium polysulphide, Captafol, Captan, Carbendazim, Carboxin, Quinone methionate (Quinomethionate), Chloroneb, Chloropicrin, Chlorothalonil, Chlozolinat, Cufraneb, Cymomanil, Cyproconazole, Cyprofuram, Dichlorophen, Diclobutrazol, Dichlofluanid, Diclomezin, Dicloran, Diethofencarb, Difenoconazol, Dimethirimol, Dimethomorph, Diniconazol, Dinocap, Diphenylamine, Dipyrithion, Ditalimfos, Dithianon, Dodine, Drazoxolon, Edifenphos, Epoxyconazole, Ethirimol, Etridiazol, Fenarimol, Fenbuconazole, Fenfuram, Fenitropan, Fenpiclonil, Fenpropidin, Fenpropimorph, Fentin acetate, Fentin hydroxide, Ferbam, Ferimzone, Fluazinam, Fludioxonil, Fluoromide, Fluquinconazole, Flusilazole, Flusulfamide, Flutolanil, Flutriafol, Folpet, Fosetyl-Aluminium, Fthalide, Fuberidazol, Furalaxyl, Furmecyclox, Guazatine, Hexachlorobenzene, Hexaconazol, Hymexazol, Imazalil, Immibenconazol, Iminoctadin, Iprobenfos (IBP), Iprodion, Isoprothiolan, Kasugamycin, copper preparations, such as: copper hydroxide, copper naphthenate, copper oxychloride, copper sulphate, copper oxide, Oxin-copper and Bordeaux mixture, Mancopper, Mancozeb, Maneb, Mepanipyrim, Mepronil, Metalaxyl, Metconazol, Methasulfocarb, Methfuroxam, Metiram, Metsulfovax, Myclobutanil, Nickel dimethyldithiocarbamate, nitrothal-isopropyl, Nuarimol, Ofurace, Oxadixyl, Oxamocarb, Oxycarboxin, Pefurazoate, Penconazol, Pencycuron, Phosdiphen, Pimaricin, Piperaline, Polyoxin, Probenazol, Prochloraz, Procymidon, Propamocarb, Propiconazole, Propineb, Pyrazophos, Pyrifenox, Pyrimethanil, Pyroquilon, Quintozen (PCNB), Sulphur and sulphur preparations, Tebuconazol, Tecloftalam, Tecnazen, Tetraconazol, Thiabendazol, Thicyofen, Thiophanate-methyl, Thiram, Tolclophos-methyl, Tolyl fluanide, Triadimefon, Triadirnenol, Triazoxid, Trichlamid, Tricyclazol, Tridemorph, Triflumizol, Triforin, Triticonazol, Validamycin A, Vinclozolin, Zineb, Ziram, 8-tert-Butyl-2-(N-ethyl-N-n-propyl-amino)-methyl-1,4-dioxa-spiro-[4,5]decane, N-(R)-(1-(4-chlorophenyl)-ethyl)-2,2-dichloro-1-ethyl-3t-methyl-1r-cyclopropanecarboxylic acid amide (mixture of diastereomers or individual isomers), [2-methyl-1-[[[1-(4-methylphenyl)-ethyl]-amino]-carbonyl]-propyl]-carbamic acid-1-methylethyl ester and 1 -methyl-cyclohexyl-1-carboxylic acid-(2,3-dichloro4-hydroxy)-anilide.

The following may be mentioned as examples of bactericides:

Bronopol, Dichlorophen, Nitrapyrin, Nickel dimethyldithio carbamate, Kasugamycin, Octhilinon, Furanecarboxylic acid, Oxytetracycline, Probenazol, Streptomycin, Tecloftalam, copper sulphate and other copper preparations.

The following may be mentioned as examples of insecticides, acaricides and nematicides:

Abamectin, Acephate, Acrinathrin, Alanycarb, Aldicarb, Alphamethrin, Amitraz, Avermectin, AZ 60541, Azadirachtin, Azinphos A, Azinphos M, Azocyclotin,

*Bacillus thuringiensis*, 4-Bromo-2-(4-chlorophenyl)-1-(ethoxymethyl)-5-(trifluoromethyl)-1H-pyrrole-3-carbonitrile, Bendiocarb, Benfuracarb, Bensultap, Betacyfluthrin, Bifenthrin, BPMC, Brofenprox, Bromophos A, Bufencarb, Buprofezin, Butocarboxin, Butylpyridaben, Cadusafos, Carbaryl, Carbofuran, Carbophenothion, Carbosulfan, Cartap, Chloethocarb, Chloretoxyfos, Chlorfenvinphos, Chlorfluazuron, Chlormephos, N-[(6-Chloro-3-pyridinyl)-methyl]-N'-cyano-N-methyl-ethanimidamide, Chlorpyrifos, Chlorpyrifos M, cis-Resmethrin, Clocythrin, Clofentezin, Cyanophos, Cycloprothrin, Cyfluthrin, Cyhalothrin, Cyhexatin, Cypermethrin, Cyromazin, Deltamethrin, Demeton-M, Demeton-S, Demeton-S-methyl, Diafenthiuron, Diazinon, Dichlofenthion, Dichlorvos, Dicliphos, Dicrotophos, Diethion, Diflubenzuron, Dimethoate, Dimethylvinphos, Dioxathion, Disulfoton, Edifenphos, Emamectin, Esfenvalerate, Ethiofencarb, Ethion, Ethofenprox, Ethoprophos, Etrimphos, Fenamiphos, Fenazaquin, Fenbutatinoxide, Fenitrothion, Fenobucarb, Fenothiocarb, Fenoxycarb, Fenpropatirin, Fenpyrad, Fenpyroximat, Fenthion, Fenvalerate, Fipronil, Fluazinam, Fluazuron, Flucycloxyron, Flucythrinat, Flufenoxuron, Flufenprox, Fluvalinate, Fonophos, Formothion, Fosthiazat, Fubfenprox, Furathiocarb, HCH, Heptenophos, Hexaflumuron, Hexythiazox, Imidacloprid, Iprobenfos, Isazophos, Isofenphos, Isoprocarb, Isoxathion, Ivermectin, Lambda-cyhalothrin, Lufenuron, Malathion, Mecarbam, Mevinphos, Mesulfenphos, Metaldehyde, Methacrifos, Methamidophos, Methidathion, Methiocarb, Methomyl, Metolcarb, Milbemectin, Monocrotophos, Moxidectin, Naled, NC 184, Nitenpyram, Omethoate, Oxamyl, Oxydemethon M, Oxydeprofos, Parathion A, Parathion M, Permethrin, Phenthoate, Phorate, Phosalon, Phosmet, Phosphamidon, Phoxim, Pirimicarb, Pirimiphos M, Pirimiphos A, Profenophos, Promecarb, Propaphos, Propoxur, Prothiophos, Prothoate, Pymetrozin, Pyrachlophos, Pyridaphenthion, Pyresmethrin, Pyrethrum, Pyridaben, Pyrimidifen, Pyriproxifen, Quinalphos, Salithion, Sebufos, Silafluofen, Sulfotep, Sulprofos, Tebufenozide, Tebufenpyrad, Tebupirimiphos, Teflubenzuron, Tefluthrin, Temephos, Terbam, Terbufos, Tetrachlorvinphos, Thiafenox, Thiodicarb, Thiofanox, Thiomethon, Thionazin, Thuringiensin, Tralomethrin, Triarathen, Triazophos, Triazuron, Trichlorfon, Triflumuron, Trimethacarb, Vamidothion, XMC, Xylylcarb, Zetamethrin.

Chemical or biological agents that induce resistance and that protect the plants against phytopathogenic microorganisms such as fungi, bacteria, viruses or viroids, may also be used as protective substances. Many compounds with a resistance-inducing action provide protection against insects or nematodes. Examples of classes of substances having a resistance-inducing action include benzothiadiazole and its derivatives, mono- and dichloroisonicotinic acids and their derivatives, dichloroisothiazole and its derivatives, dibromothiophencarboxylic acids and their derivatives, salicylic acid and its derivatives, as well as Probenazole. Biological resistance-inducing agents include microorganisms, for example fungi, bacteria or viruses useful to the plant, and which provide protection for the plant against pathogenic organisms, for example against harmful fungi, bacteria, viruses or nematodes.

In addition to such microorganisms, there may also be used in the artificial seeds according to the invention organisms that act as symbionts, for example mycorrhizal-fungi, or that promote plant growth, like for example rhizobia in connection with nitrogen fixation. Also, by the formation of specific metabolic products by microorganisms that are used in combination with the plant material, the germination and growth of the plants can be improved and the plants can be protected against pathogens and attack by pests.

The hydrogel embedding compositions according to the invention can be used as a way of storing or transporting biological material.

The invention also provides for the use of the resultant embedded biological materials as artificial seeds.

The biodegradability of the polyester polyurethane polyureas according to the invention as well as the mixtures with the polysaccharide derivatives according to the invention was demonstrated as described hereinafter. The biodegradability of the embedding compositions formed from the materials according to the invention was also demonstrated in compost and soil. The material had completely degraded after at most 4 weeks, a control experiment with a biologically inactive substrate did not show any decomposition, and accordingly a disintegration of the embedding composition by hydrolysis or mechanical influences can be excluded. The degradation also occurred in the presence of the specified additives according to the invention, for example active constituents, nutrients, etc.

The compounds to be tested are buried in a 2 cm-high mixture of completely rotted compost from a composting unit, degree of rotting IV, in a suitable box. The filled boxes are incubated in an incubating cabinet for in each case 4 weeks in succession at 60°, 50° and 37° C. Water losses are determined from the weight loss and are replenished. During incubation the pH of the compost is regularly measured. If the measured value deviates by more than 1 unit from pH 7, the pH is readjusted to 7.0 by adding 100 mM potassium phosphate. At weekly intervals incubation of a batch is discontinued, the materials are removed, purified, dried to constant weight at 80° C., and photographed. Immediately after drying the weight loss of the material was determined by renewed weighing.

In the poisoned control, the incubation batch is completely dried at 105° C. and the evaporated water is then replaced by a 0.1% $HgCl_2$ solution. The samples for the poisoned control are placed in the $HgCl_2$ solution and then dried, before being added to the compost mixture. The control batch is incubated in exactly the same way as the batches to be tested. A substance is classified as biodegradable if, after 4 weeks, sample substances can no longer be detected in the unpoisoned batch whereas the sample in the poisoned batch remains unchanged.

The invention will now be illustrated in more detail with the aid of the following examples, though without being restricted by the latter.

EXAMPLES

In the examples the polyester polyurethane polyurea according to DE 19 517 185, now U.S. Pat. No. 5,961,906 is used as polyester polyurethane polyurea. Water-soluble, biodegradable hydroxyalkyl cellulose ethers with a mean molecular weight (number average) of ca. 10000 to 200000 g/mole and a degree of substitution as regards the ether groups of ca. 0.5 to 1.5 are used as hydroxyethyl cellulose or hydroxypropyl cellulose in the examples.

Example 1

Potato plants (*Solanum tuberosum*) were propagated in vitro. For this purpose shoot cuttings with 2 to 6 small leaves were placed in liquid BM medium containing 20 g/l of sucrose and incubated in a plant cabinet under a light/dark rhythm of 12 hours each at 22° C. during the day-time and 19° C. during the night-time. The BM medium consisted of salts according to Murashige/Skoog (cf. Murashige T., Skoog, Physiol. Plant. 15, 473–479, 1962) and vitamins corresponding to Gamborg's Medium B5 (Gamborg O. L., Miller R. A., Ojima K., Exp. Cell. Res. 50, 151, 1968, Gamborg O. L., Murashige T., Thorpe T. A., Vasil I. K., In Vitro 12 473, 1976). After 3 to 4 weeks shoot cuttings were taken from these plants and used for encapsulation experiments.

The shoot cuttings were suspended under sterile conditions in a 3% dispersion of hydroxypropyl cellulose (HPC; with addition of 0.2 M $CaCl_2$ in semi-concentrated nutrient solution according to Murashige-Skoog) and added dropwise while stirring to a 1% alginate solution. The spheres were next washed, while stirring, with a 0.2 M $CaCl_2$ solution. The spheres were then added while gently stirring to a 5% aqueous dispersion of polyester polyurethane polyurea, a thin, elastic coating of polyester polyurethane polyurea forming on the surface of the sphere.

After 5 minutes the spheres, which now had a diameter of ca. 5 mm, were removed from the solution and washed with 0.2 M $CaCl_2$ solution. The spheres were then laid out for germination on agar plates containing semi-concentrated Murashige-Skoog nutrient medium. Incubation was carried out at 20° C. under 12 hours' light per day in a plant cabinet.

After ca. 2 to 3 weeks small plants were growing on the polymer spheres. The germination rate was 66%.

Example 2

The biological material to be encapsulated and derived from potato plants (cultivated according to Example 1) was suspended under sterile conditions in a 3% solution of sodium alginate. The suspension was added dropwise to a 0.2 M $CaCl_2$ solution, resulting in the formation of alginate spheres. After 30 minutes the spheres were suctioned off and added to a gently stirred 5% aqueous polyester polyurethane polyurea dispersion. A thin elastic coating of polyester polyurethane polyurea formed on the surface of the alginate hydrogels. After 5 minutes the spheres were removed from the solution and if necessary washed once more in a 0.1 M $CaCl_2$ solution. For germination, the seeds, which had a diameter of ca. 5 mm, were placed on agar plates with semi-concentrated Murashige-Skoog nutrient medium. Incubation was carried out, as described in Example 1, in the plant cabinet.

Example 3

75 ml of a 40% dispersion of a polyester polyurethane polyurea and 75 ml of a 2% dispersion of hydroxyethyl cellulose are each autoclaved individually at a temperature of 121° C. for 20 minutes and then mixed under sterile conditions in a ratio of 1:1.

The potato shoot cuttings were applied under sterile conditions to the surface of this mixture of hydroxyethyl cellulose and polyester polyurethane polyurea and sucked off individually by means of a pipette.

The shoot cuttings together with the surrounding mixture of hydroxyethyl cellulose and polyester polyurethane polyurea are then added dropwise to a 0.2 M $CaCl_2$ solution. After a residence time of 10 minutes the spheres, which have a diameter of ca. 5 mm, were removed and laid out on agar with semi-concentrated MS medium. Incubation was carried out at 20° C. under 12 hours' illumination per day in the plant cabinet. The ger mination rate was 9 0% within 2 to 3 weeks.

Example 4

75 ml of a 40% dispersion of a polyester polyurethane polyurea and 75 ml of a 2% dispersion of hydroxypropyl cellulose were each autoclaved individually at a temperature of 121° C. for 20 minutes and then mixed under sterile conditions in a ratio of 1:1.

The potato plants were propagated in vitro (cf. Example 1). After 3 to 4 weeks shoot cuttings were taken from these plants and used for encapsulation experiments. The shoot cuttings were placed under sterile conditions on the surface of the mixture of hydroxypropyl cellulose and polyester polyurethane polyurea and sucked off individually by means of a pipette.

The shoot cuttings together with the surrounding mixture of hydroxypropyl cellulose and polyester polyurethane polyurea were then added dropwise to a 0.2 M $CaCl_2$ solution. After a residence time of 10 minutes the spheres, which have a diameter of ca. 5 mm, were removed and placed on agar with semi-concentrated MS medium.

Incubation was carried out at 20° C. under 12 hours' illumination per day in the plant cabinet. The germination rate was between 90% and 100% within 2 to 3 weeks.

Example 5

A cell suspension of carrots (*Daucus carota*) was incubated in 50 ml of hormone-containing Murashige-Skoog medium (MS medium, cf. Murashige T., Skoog, F., Physiol. Plant. 15, 473–479, 1962) at 25° C. and 100 revs. per minute on a mechanical shaker in the dark.

After 8 days 150 ml of the cell suspension was screened through a sieve of mesh width 500 $\mu$m, 75 $\mu$m and 30 $\mu$m. The 30 $\mu$m to 75 $\mu$m cell fraction was rinsed with hormone-free medium, sedimented by centrifugation at 100 g, washed twice with hormone-free MS medium and, after renewed centrifugation, taken up in 20 ml of hormone-free MS medium. The cell count was as a rule $0.5 \times 10^4$ to $10^5$ cells/ml.

These cells were used to induce embryogenesis. The screened, washed cells were, as described above, incubated further on the mechanical shaker; after 2 days and 5 days there was a change of medium, the cells being centrifuged off and resuspended in hormone-free MS medium. The cells were then incubated for a further 9 days. After a total of 14 days the suspension contained 10 to 100 embryoids/ml.

Somatic carrot embryos of the "torpedo" and "cotelydonary" stages were applied to the surface of a mixture of hydroxypropyl cellulose and polyester polyurethane polyurea. The embryos were sucked off individually using a pipette and added dropwise together with the surrounding polymer mixture to a 0.2 M $CaCl_2$ solution. After a residence time of 10 minutes the spheres, which have a diameter of ca. 5 mm, were removed and placed on agar with semi-concentrated MS medium. The incubation was carried out at 20° C. under 12 hours' illumination per day in the plant cabinet. After 2 weeks 20% of the spheres had germinated.

Example 6

Examination of the biodegradability of the encapsulations.

The encapsulations obtained from Examples 1–5 were, as described hereinbefore, tested in a composting experiment as regards their complete biodegradability. The degradation was checked at intervals of a few days. The control experiment in poisoned compost shows that microbial decomposition takes place.

| Example | 7 days | 20 days | 32 days | 42 days | Control |
|---|---|---|---|---|---|
| 1 | intact | discoloured | incipient decomposition | decomposed | intact |
| 2 | intact | discoloured | incipient decomposition | decomposed | intact |
| 3 | intact | discoloured | incipient decomposition | decomposed | intact |
| 4 | intact, discoloured | discoloured | incipient decomposition | decomposed | intact |
| 5 | intact, discoloured | discoloured | incipient decomposition | decomposed | intact |

Example 7

75 ml of a 40% dispersion of a polyester polyurethane polyurea and 75 ml of a 2% dispersion of hydroxypropyl cellulose which additionally contains 2% of Imidacloprid were each autoclaved individually at a temperature of 121° C. for 20 minutes and then mixed under sterile conditions in a ratio of 1:1. This mixture was added dropwise to a 0.2 M $CaCl_2$ solution.

The resulting ca. 5 mm large spheres contain ca. 30 mg/g of the active constituent.

Example 8

Drying/rehydration.

The shperes prepared in Examples 1 to 5 were dried for 7 days under normal atmospheric conditions and then weighed. After 24 hours' storage in water, a weight increase of around 45% was measured, which did not increase any further even after prolonged storage in water.

Example 9

Combination with active components.

75 ml of a 40% dispersion of a polyurethane polyurea and 75 ml of a 2% dispersion of hydroxypropyl cellulose were each autoclaved individually at a temperature of 121° C. for 20 minutes and then mixed under sterile conditions in a ratio of 1:1.

A solution of the herbicide Imidacloprid (1 mole/l in DMF) was sterile filtered through a membrane filter (pore width 0.2 μm) and then diluted 1:10 with sterile water. The resultant stock suspension of Imidacloprid was added to the mixture of polyurethane polyurea and hydroxypropyl cellulose to give an end concentration of 0.1 mM/l. A sterile 0.2 M $CaCl_2$ solution contains Imidacloprid in the same end concentration.

The potato shoot cuttings (cf. Example 1) were placed under sterile conditions on the surface of the mixture of hydroxypropyl cellulose and polyurethane polyurea and sucked off individually by means of a pipette.

The shoot cuttings together with the surrounding mixture of hydroxypropyl cellulose and polyurethane polyurea were then added dropwise to a 0.2 M $CaCl_2$ solution. Potato shoot cuttings without Imidacloprid were encapsulated as a control test. After a residence time of 10 minutes the spheres were removed and placed on agar with semi-concentrated MS medium. Incubation was carried out at 20° C. under 12 hours' illumination per day and 70% atmospheric humidity in the plant cabinet.

The germination rate was 64% within 4 weeks; the control without Imidacloprid showed a germination rate of 57%.

What is claimed is:

1. A hydrogel comprising:
   A) at least one polyester polyurethane polyurea,
   B) at least one polysaccharide, a derivative thereof, or a mixture thereof, and
   C) at least one biological material.

2. The hydrogel of claim 1, wherein C) said biological material comprises biological plant material that is capable of dividing.

3. The hydrogel of claim 2, wherein C) said biological plant material is selected from the group consisting of (1) plant cells, (2) callus tissue, (3) protoplasts, (4) plant tissue, (5) plant organs, (6) zygotic embryos (7) somatic embryos and (8) protocrom analogues.

4. The hydrogel of claim 3, wherein C)(5) the plant organs comprise adventitious shoots, micronodules, auxiliary buds, apical buds and/or scions.

5. The hydrogel of claim 1, wherein C) said biological material is capable of dividing from transgenic plants.

6. The hydrogel of claim 1, wherein A) the polyester polyurethane polyurea comprises the reaction product of a) an organic diisocyanate component, with b) a diol component, c) a diamine component, and optionally, d) a hydrophilic polyether alcohol, optionally, in the presence of e) water, wherein the water is not included in the calculation of the equivalent ratio of isocyanate groups to isocyanate-reactive groups.

7. The hydrogel of claim 6, wherein A) the polyester polyurethane polyurea is prepared from a) an organic diisocyanate component which is selected from the group consisting of a)1) hexamethylene diisocyanate, and a)2) a mixture of hexamethylene diisocyanate with a total of up to 60% by weight, based on 100% by weight of the mixture, of at least one compound selected from the group consisting of (i) 1-isocyanato-3,3,5-trimethyl-5-isocyanatomethyl-cyclohexane, (ii) 4,4'-diisocyanatodicyclohexylmethane, and (iii) 1-methyl-2,4(6)-diisocyanatocyclohexane.

8. The hydrogel of claim 1, wherein B) the polysaccharide and/or derivative thereof comprises at least one compound selected from the group consisting of soluble starch, alginates, methyl cellulose, hydroxyethyl cellulose, methylhydroxypropyl cellulose, methylhydroxyethyl cellulose, hydroxylpropyl cellulose, and mixtures thereof.

9. The hydrogel of claim 1, which additionally comprises one or more of the following components: a suitable nutrient salt mixture for plant breeding, a bactericidal constituent, a fungicidal constituent, an insecticidal constituent, an acaricidal constituent, a nematicidal constituent, a resistance-inducing constituent, and a herbicidal active constituent.

10. An artificial seed comprising the hydrogel of claim 1.

11. An embedding composition for biological materials, wherein the embedding composition comprises A) at least one polyester polyurethane polyurea, and B) at least one polysaccharide, a derivative thereof, or a mixture thereof.

12. The embedding composition of claim 11, which comprises an aqueous dispersion of A) 5 to 50% by weight of at least one polyester polyurethane polyurea, and B) 0.1% by weight or more of at least one polysaccharide, a derivative thereof, or a mixture thereof.

13. A process for the production of a biological material embedded in a hydrogel comprising 1) mixing the biological material in the presence of an aqueous dispersion of a polyester polyurethane polyurea, with a polysaccharide, a derivative thereof or a mixture thereof, and 2) coacervating the mixture formed in step 1) by contact with a salt solution.

14. The process of claim 13, wherein the salt solution in step 2) comprises a salt solution of polyvalent ions.

* * * * *